(12) United States Patent
Suri et al.

(10) Patent No.: US 6,180,799 B1
(45) Date of Patent: Jan. 30, 2001

(54) SULFALATION OF TETRAOL

(75) Inventors: Suresh C. Suri, Lancaster, CA (US);
Stephen L. Rodgers, Fairfax, VA (US)

(73) Assignee: The United States of America as represented by the Secretary of the Air Force, Washington, DC (US)

( * ) Notice: Under 35 U.S.C. 154(b), the term of this patent shall be extended for 0 days.

(21) Appl. No.: 09/562,081

(22) Filed: May 1, 2000

(51) Int. Cl.$^7$ .................................................. C07D 327/10

(52) U.S. Cl. ............................................................... 549/18

(58) Field of Search .................................................. 549/18

(56) References Cited

U.S. PATENT DOCUMENTS

| | | | | |
|---|---|---|---|---|
| 2,471,274 | * | 5/1949 | Lingo | 549/18 |
| 2,587,641 | * | 4/1952 | Moersch et al. | 549/18 |
| 4,924,007 | * | 5/1990 | Massonneau et al. | 549/18 |
| 5,116,999 | * | 5/1992 | Le Roy et al. | 549/18 |

* cited by examiner

*Primary Examiner*—Amelia Owens
(74) *Attorney, Agent, or Firm*—Thomas C. Stover

(57) ABSTRACT

Provided are novel methods for preparing pentaerythritol disulfite employing reduced amounts of thionyl chloride and 1,2-dichloroethane as reaction media. Also disclosed is the first synthesis of pentaerythritol disulfate by oxydation of the above pentaerythritol disulfite. Both the disulfite (2) and the disulfate (3) are obtained in high yields.

3 Claims, No Drawings

SULFALATION OF TETRAOL

RELATED APPLICATIONS

None

STATEMENT OF GOVERNMENT INTEREST

The invention described herein may be manufactured and used by or for the Government for governmental purposes without the payment of any royalty thereon.

FIELD OF THE INVENTION

This invention relates to methods of preparing disulfites and disulfates particularly pentaerythritol disulfite and disulfate.

BACKGROUND OF THE INVENTION

The literature methodology for pentaerythritol disulfite requires thionyl chloride as a reagent and as a reaction media or solvent. This means excessive use of thionyl chloride that is corrosive, expensive and lachrymose. Such prior art method thus suffers problems in handling of thionyl chloride, scale-up and cost.

As for pentaerythritol disulfate it has been reported in the literature in a low yield (17%) but no procedure is given in an Article by H. Gulyas et al in J. Chem. Soc. Chem. Comm., 1997, 2385.

Accordingly there is need and market for preparation of the above compounds that overcomes the above prior art shortcomings.

There has now been discovered a method for preparation of the above compounds that avoids excessive use of thionyl chloride with improved handling and at reduced cost.

SUMMARY OF THE INVENTION

Broadly, the present invention provides an inventive method for preparing pentaerythritol disulfite (2) from pentaerythritol (1) and an inventive method for preparing pentaerythritol disulfate (3) from 2, according to the following reaction scheme.

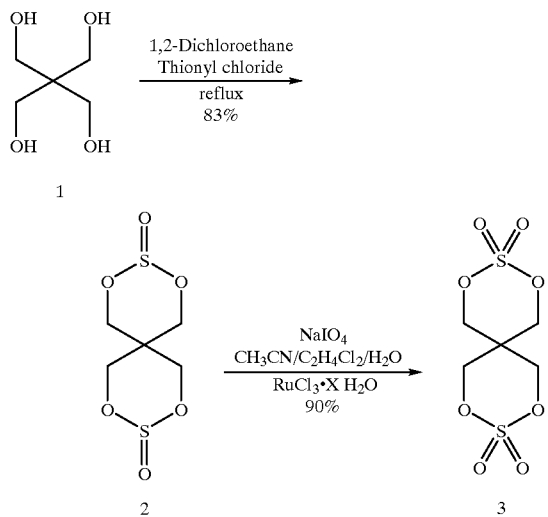

The invention will become more apparent from the following detailed specification given below.

DESCRIPTION OF PREFERRED EMBODIMENTS

The problems of the prior synthesis of 2 are overcome by reacting compound 1 with just over stoichiometric amounts of thionyl chloride (e.g., 1.5 equivalent/diol) in 1,2 dichloroethane solvent according to the first step of the above scheme, to yield up to 83 wt %.

Thereafter, compound 2 is oxidized with ruthenium tetroxide that is generated in situ from ruthenium trichloride hydrate/sodium periodate according to the second step of the above scheme in a yield of up to 90 wt % or more.

The following examples are given in illustration of the methods of the present invention and should not be construed in limitation thereof.

EXAMPLE I

Synthesis of Pentaerythritol Disulfite (2): Pentaerythritol (1, 13.6 g, 100 mmol) and activated molecular sieves (10.0 g) were suspended in dry 1,2-dichloroethane (180 mL) in three-necked round-bottom flask (500 mL). The flask was fitted with gas dispersion tube, pressure equalizing addition funnel and reflux condenser. The condenser was attached to a nitrogen bubbler and a refrigerating circulator at −3° C. Freshly distilled thionyl chloride (37.7 g, 300 mmol, 21.9 mL) taken in a pressure-equalizing addition funnel, was added to a reaction flask at reflux temperature (80° C.) with continuous slow nitrogen purging during a period of 0.5 hr. The reaction mixture was refluxed overnight (~16 hrs). The completion of the reaction was judged by homogeneity of the reaction mixture (no suspension of pentaerythritol) and absence of hydrochloric gas (checked with ammonia solution) coming out of the reaction flask. The reaction mixture was filtered while hot through a Buchner funnel. The filtrate was concentrated to furnish crystallized pentaerythritol disulfite ( 2, 19 g), m. p. 150° C., in 83 wt % yield. The pentaerythritol disulfite was identified by spectral and analytical data. The spectral characteristics are: IR(KBr) ν 1465, 1453, 1401, 1193, 1182, 1179, 968, 759 cm$^{-1}$; Analysis calculated for $C_5H_8O_6S_6$: C=26.31; H=3.53. Found: C=26.40; H=3.65.

EXAMPLE II

Synthesis of Pentaerythritol Disulfate (3): To a solution of pentaerythritol disulfite (2, 4.56 g, 20 mmol) and sodium periodate (12.8 g, 60 mmol) in acetonitrile/1,2-dichloroethane/water (140 mL; 1:1:1.5) in a round-bottom flask immersed in ice-water bath, was added ruthenium trichloride hydrate(83 mg, 0.4 mmol, 2 mole %). The temperature of the reaction mixture was around 5° C. The reaction mixture was stirred for 2 hr at the same temperature when thin layer chromatography indicated the consumption of pentaerythritol disulfite. The reaction mixture was filtered through a sintered funnel. The filterand was washed with hot acetonitrile (2×50 mL). The combined filtrate was taken in a separatory funnel and extracted with ethylacetate (2×10 mL). The ethyl acetate layer was washed with water and brine. The organic layer was dried over anhydrous magnesium sulfate. Removal of the solvent furnished solid that crystallized from acetonitrile to furnish pentaerythritol disulfate ( 3, 4.7g), m.p. 270° C., in 90 wt % isolated yield. The pentaerythritol disulfate was identified by spectral and analytical data. The spectral characteristics are: IR (KBr) ν 3047, 2978, 1454, 1407, 1200, 1145, 1034, 938, 819, 774 cm$^{-1}$; Analysis calculated for $C_5H_8O_8S_2$: C=23.19; H=3.10. Found: C=23.19; H=3.20.

A novel aspect of the present invention is the synthesis of pentaerythritol disulfite that requires thionyl chloride as a reagent and not as a solvent. The disappearance of pentaerythritol suspension in 1,2-dichloroethane indicates its complete conversion into pentaerythritol disulfite that crystallizes out from the solvent (1,2-dichloroethane) on concentration, as indicated in Example 1.

Also the second embodiment of the invention, disclosed herein, is believed to be the first synthesis of pentaerythritol disulfate by oxidation of pentaerythritol disulfite using Sharpless reagent with modified procedure.

The present invention thus provides low cost and efficient methods for preparing the above compounds as precursors to a variety of future compounds having energetic properties. Because of the anti-oxidant property of cyclic sulfite class of compounds, pentaerythritol disulfite can stablize organic compounds and polymers against thermal decomposition. Also pentaerythritol disulfate is a potential precursor for the compounds that can be used as energetic additives in propellants, e.g., (a) spiro[2.2]pentane; (b) 2,6-dioxaspiro [3.3]heptane; (c) 3,6-diazaspiro[3.3]heptane; (d) N,N-dinitro-3,6-diazaspiro[3.3]heptane; (e) tetrakis (azidomethyl)methane; (f) tetrakis(aminomethyl)methane; (g) tetrakis(propargyl)methane; (h) pentaerythritol tetranitrate (PETN); (i) Dendrimers using different building blocks; and (j) spirosurfactants and phospholipids and the like.

Thus the invention is believed to have major improvements over the prior synthetic methodology in terms of handling, scale-up and costs.

What is claimed is:
1. A method for preparing pentaerythritol disulfite comprising the following reaction sequence.

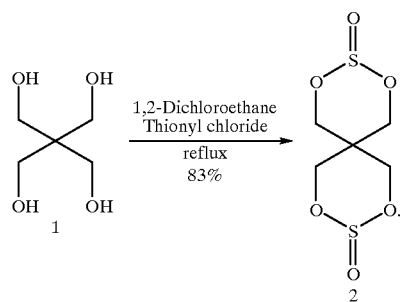

2. The method of claim 1 employing a slight excess of stoichiometric amounts of thionyl chloride and using 1,2-dichloroethane as solvent.

3. A method for preparing pentaerythritol disulfate comprising the following reaction sequence.

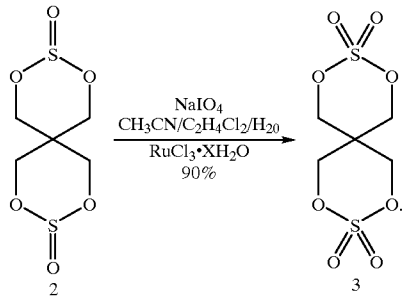

* * * * *